US012582317B2

(12) United States Patent
Fukagawa

(10) Patent No.: US 12,582,317 B2
(45) Date of Patent: Mar. 24, 2026

(54) DETECTING DEVICE AND MEASURING APPARATUS

(71) Applicant: SEIKO EPSON CORPORATION, Tokyo (JP)

(72) Inventor: Takefumi Fukagawa, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 547 days.

(21) Appl. No.: 18/173,794

(22) Filed: Feb. 24, 2023

(65) Prior Publication Data

US 2023/0270332 A1      Aug. 31, 2023

(30) Foreign Application Priority Data

Feb. 28, 2022      (JP) ................................. 2022-029137

(51) Int. Cl.
*A61B 5/00*          (2006.01)
*A61B 5/02*          (2006.01)
(Continued)

(52) U.S. Cl.
CPC ........ *A61B 5/0059* (2013.01); *A61B 5/02108* (2013.01); *A61B 5/1455* (2013.01); *H10K 59/60* (2023.02); *A61B 5/02416* (2013.01); *A61B 5/14532* (2013.01); *A61B 5/14551* (2013.01); *A61B 5/681* (2013.01);
(Continued)

(58) Field of Classification Search
CPC .............. A61B 5/0059; A61B 5/02108; A61B 5/02141; A61B 5/02416; A61B 5/14532; A61B 5/1455; A61B 5/14551; A61B 5/14552; A61B 5/681; A61B 5/7405;

A61B 5/7445; A61B 5/7455; A61B 2562/0233; A61B 2562/046; G01J 1/0209; G06F 2218/00; H10K 59/30; H10K 59/60
See application file for complete search history.

(56) References Cited

U.S. PATENT DOCUMENTS

2015/0282739 A1*  10/2015  Nishida .................. A61B 5/489
                                                              600/316
2016/0089063 A1*   3/2016  Nishida ................ A61B 5/1455
                                                              600/316

FOREIGN PATENT DOCUMENTS

CN          108604296        9/2018
JP          2005092006        4/2005
(Continued)

OTHER PUBLICATIONS

Translation of WO 2017-188715 (Year: 2017).*
Translation of JP 2005-092006 (Year: 2005).*
Translation of JP 2013-009709 (Year: 2013).*

*Primary Examiner* — Mark R Gaworecki
(74) *Attorney, Agent, or Firm* — JCIPRNET

(57) ABSTRACT

A detecting device includes a substrate and a plurality of detecting elements arranged in a matrix at the substrate. Each of the plurality of detecting elements includes a light emitting portion and a light receiving portion that receives light of a wavelength emitted from the light emitting portion at a position adjacent to the light emitting portion. The light receiving portion includes a photoelectric conversion portion formed at the substrate. The light emitting portion includes an organic EL light emitting element formed at the substrate. The area of the light receiving portion is larger than the area of the light emitting portion.

12 Claims, 7 Drawing Sheets

(51) Int. Cl.

| | | |
|---|---|---|
| *A61B 5/021* | (2006.01) | |
| *A61B 5/1455* | (2006.01) | |
| *H10K 59/60* | (2023.01) | |
| *A61B 5/024* | (2006.01) | |
| *A61B 5/145* | (2006.01) | |
| *H10K 59/30* | (2023.01) | |

(52) U.S. Cl.
CPC . *A61B 2562/0233* (2013.01); *A61B 2562/046* (2013.01); *G06F 2218/00* (2023.01); *H10K 59/30* (2023.02)

(56) References Cited

FOREIGN PATENT DOCUMENTS

| | | | | | |
|---|---|---|---|---|---|
| JP | 2005092006 | A | * | 4/2005 | |
| JP | 2013009709 | | | 1/2013 | |
| JP | 2013009709 | A | * | 1/2013 | |
| JP | 2016122004 | | | 7/2016 | |
| JP | 2018061675 | | | 4/2018 | |
| WO | WO-2017188715 | A2 | * | 11/2017 | ......... G06V 40/1318 |

* cited by examiner

DETECTING DEVICE AND MEASURING APPARATUS

The present application is based on, and claims priority from JP Application Serial Number 2022-029137, filed Feb. 28, 2022, the disclosure of which is hereby incorporated by reference herein in its entirety.

BACKGROUND

1. Technical Field

The present disclosure relates to a detecting device and a measuring apparatus including a light emitting portion and a light receiving portion.

2. Related Art

Various measurement techniques for non-invasively measuring biological information such as a heartbeat have been proposed. JP-A-2018-061675 and JP-A-2016-122004 describe a detecting device including a light emitting portion that emits light toward a living body and a light receiving portion that receives light reflected by the living body. Biological information can be obtained by analyzing a signal output from the light receiving portion in this type of detecting device.

The detecting device of JP-A-2018-061675 includes a substrate, on whose surface a light emitting element and a light receiving element are arranged, and a shielding member that covers the substrate. The shielding member includes a reflecting portion that reflects light from the light emitting element toward the living body and a light-blocking portion positioned between the light emitting element and the light receiving element. Installing the light-blocking member increases the light utilization efficiency of the light emitting portion while dealing with stray light for the light receiving portion.

The detecting device of JP-A-2016-122004 includes a light source (a light emitting portion) surrounded by a light-blocking member and a light receiving portion (a spectral sensor) shielded from the light source by the light-blocking member. The light source includes, for example, an LED. The spectroscopic sensor includes a plurality of photodiodes arranged on a substrate, an angle limiting filter formed at each of the photodiodes, and a bandpass filter formed at the angle limiting filter. The light-blocking member, the angle limiting filter, and the bandpass filter prevent detection of light other than light to be measured.

The detecting devices of JP-A-2018-061675 and JP-A-2016-122004 can increase detection accuracy by preventing unnecessary light from being incident on the light receiving portion. However, there is a limit to a reduction in the size due to the configuration in which the shielding member and the filter are provided.

SUMMARY

To solve the above problems, a detecting device of the present disclosure includes a substrate and a plurality of detecting elements arranged in a matrix at the substrate, wherein each of the plurality of detecting elements includes a light emitting portion configured to emit light toward a living body and a light receiving portion configured to receive light from the living body based on the light emitted from the light emitting portion, the light receiving portion includes a photoelectric conversion portion formed at the substrate, and the light emitting portion includes an organic electroluminescent light emitting element formed at the substrate at a position adjacent to the photoelectric conversion portion.

A measuring apparatus of the present disclosure includes the above detecting device and an information analysis unit configured to identify biological information from a detection signal indicating a detection result of the detecting device.

DESCRIPTION OF EXEMPLARY EMBODIMENTS

Figure 1:
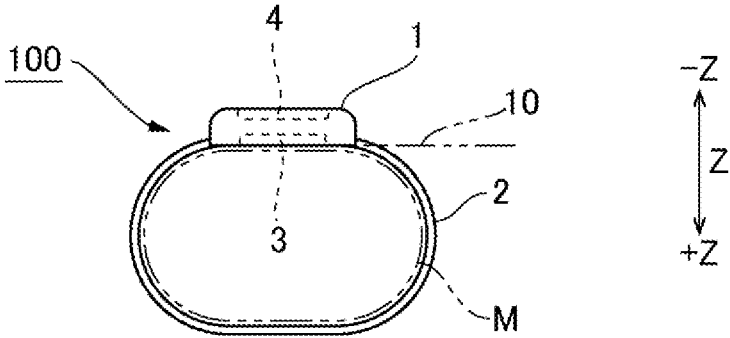
FIG. 1 is a side view of a measuring apparatus according to a first embodiment.

Hereinafter, embodiments of the present disclosure will be described with reference to the drawings. In each drawing below, each member is schematically shown as having a recognizable size and actual dimensions and ratios thereof may differ from those shown in the drawings.

1. First Embodiment

Measuring Apparatus

FIG. 1 is a side view of a measuring apparatus 100 of a first embodiment. The measuring apparatus 100 is a biometric device that non-invasively measures biological information. The measuring apparatus 100 is used oriented toward a site (hereinafter referred to as a "measuring site M") that is a measurement target on a body of a subject (a living body). In an example shown in FIG. 1, the measuring apparatus 100 is a wristwatch-type portable device that includes a housing 1 and a belt 2. The measuring site M is a wrist of the subject. The measuring apparatus 100 is used worn on the wrist (the measuring site M) of the subject by winding the belt 2 around the wrist with a detecting surface 10 of the housing 1 facing a skin surface of the wrist.

In the present specification, an X direction, a Y direction, and a Z direction are directions orthogonal to each other. The X direction is a first direction. The Y direction is a second direction. The Z direction is a direction normal to the detecting surface 10. A +Z direction is a direction from the detecting surface 10 to the measuring site M. A −Z direction is a direction from the measuring site M to the detecting surface 10.

In the present specification, biological information is exemplified by a heartbeat (for example, a pulse rate) and an oxygen saturation (SpO$_2$) of the subject. The heartbeat indicates the change of the internal volume of a blood vessel over time due to the pulsation of the heart. The oxygen saturation indicates the proportion (%) of hemoglobin bound to oxygen in hemoglobin in the blood of the subject and is an index for evaluating the respiratory function of the subject.

Figure 2:
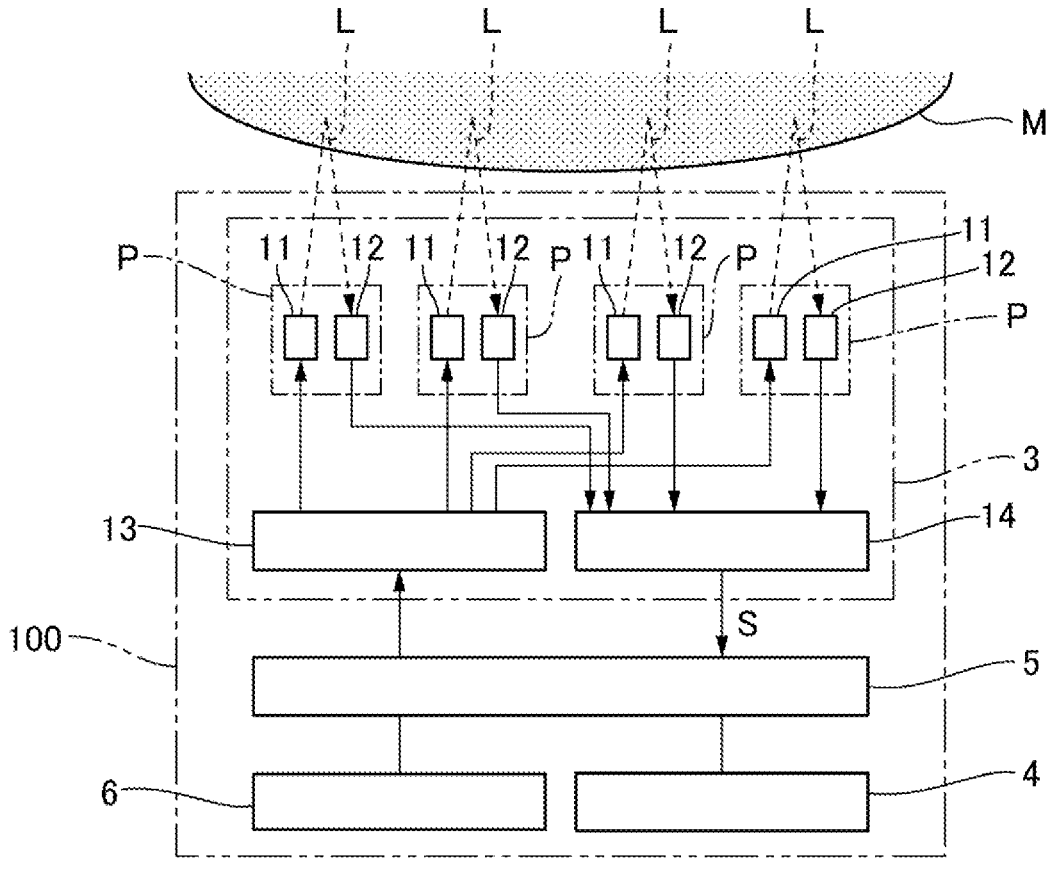
FIG. 2 is a block diagram showing functional components of the measuring apparatus of the first embodiment.

FIG. 2 is a block diagram showing functional components of the measuring apparatus 100 of the first embodiment. The measuring apparatus 100 includes a control device 5, a storage device 6, a display device 4, and a detecting device 3. The control device 5 and the storage device 6 are disposed inside the housing 1. The detecting device 3 is disposed on the detecting surface 10. The display device 4 is disposed on a surface of the housing 1 opposite to the detecting surface 10. The display device 4 displays various images including measurement results under the control of the control device 5. The display device 4 is, for example, a liquid crystal display panel.

In addition to the functional components shown in FIG. 2, the measuring apparatus 100 may include an operation unit such as an operation button or a touch panel disposed on the surface of the housing 1 and may be configured to input an operation signal corresponding to an operation on the operation unit to the control device 5. The measuring apparatus 100 may also include a communication unit for outputting measurement results to the outside and inputting a signal from the outside to the control device 5. Alternatively, the measuring apparatus 100 may include an audio output unit or a vibrating unit as means for notifying of measurement results.

As shown in FIG. 2, the detecting device 3 includes light receiving portions 11, light emitting portions 12, a drive circuit 13, and an output circuit 14. One or both of the drive circuit 13 and the output circuit 14 can be installed as circuits external to the detecting device 3. That is, the drive circuit 13 and the output circuit 14 may be omitted from the detecting device 3.

The detecting device 3 is a reflective optical sensor module that emits light through the detecting surface 10 and receives light that has been incident on the detecting surface 10 from the measuring site M to generate a detection signal S. That is, in the detecting device 3 of the first embodiment, the light receiving portions 11 and the light emitting portions 12 are disposed on the detecting surface 10. The drive circuit 13 supplies a driving current to each light emitting portion 12 to cause it to emit light. Light emitted from a light emitting portion 12 is incident on the measuring site M through the detecting surface 10 and propagates in the measuring site M while being repeatedly reflected and scattered and is then emitted from the measuring site M and incident on a light receiving portion 11 disposed on the detecting surface 10.

The light receiving portions 11 and the light emitting portions 12 are arranged in pairs on the detecting surface 10. The detecting device 3 includes a plurality of detecting elements P each having one light receiving portion 11 and one light emitting portion 12. Light L emitted from the light emitting portion 12 of each detecting element P is, for example, green light having a green wavelength band of 520 nm to 550 nm and a peak wavelength of 520 nm. The wavelength of light emitted from the light emitting portion 12 is not limited to that of this wavelength band.

The light receiving portion 11 of each detecting element P receives light L that has been emitted from the light emitting portion 12 in the same detecting element P and then returned to the detecting surface 10 after being repeatedly reflected and scattered in the measuring site M. The light receiving portion 11 generates a detection signal corresponding to the intensity of the received light. The output circuit 14 is configured to include, for example, an A/D converter that converts the detection signal generated by the light receiving portion 11 from analog to digital and an amplifier circuit that amplifies the converted detection signal (both not shown) and generates a detection signal S representing the intensity of light received by the light receiving portion 11.

The detection signal S is a heartbeat signal including periodic fluctuations corresponding to pulsations (volume heartbeats) of the artery inside the measuring site M because the amounts of light absorbed by blood during dilation and contraction of blood vessels generally differ.

The drive circuit 13 and the output circuit 14 are mounted, for example, on a substrate in the form of an IC chip. In the first embodiment, the drive circuit 13 is mounted on a substrate 20 (see FIG. 3) on which the plurality of detecting elements P are formed as will be described later. The output circuit 14 may be mounted on the substrate 20 on which the detecting elements P are formed together with the drive circuit 13 or may be mounted on a separate substrate. Alternatively, the output circuit 14 may be installed as a circuit external to the detecting device 3.

The control device 5 is an arithmetic processing unit such as a central processing unit (CPU) or a field-programmable gate array (FPGA) and controls the entirety of the measuring apparatus 100. The storage device 6 includes, for example, a non-volatile semiconductor memory and stores a program executed by the control device 5 and various data used by the control device 5. It is also possible to adopt a configuration in which the functions of the control device 5 are distributed over a plurality of integrated circuits or a configuration in which some or all of the functions of the control device 5 are realized by a dedicated electronic circuit. Although the control device 5 and the storage device 6 are shown as separate elements in FIG. 2, a control device 5 including the storage device 6 can also be realized, for example, by an ASIC.

The control device 5 identifies biological information of the subject from the detection signal S generated by the detecting device 3 by executing the program stored in the storage device 6. The control device 5 identifies a heartbeat of the subject from the detection signal S representing the intensity of light received by the light receiving portion 11. The control device 5 can identify, for example, the pulse rate of the subject based on the detection signal S.

The control device 5 functions as an information analysis unit that identifies biological information from the detection signal S indicating the detection result of the detecting device 3 as described above. The control device (information analysis unit) 5 causes the display device 4 to display the biological information identified from the detection signal S. It is also possible to notify the user of the measurement result by voice output. It is also possible to notify the user of a warning (possibility of impaired physical function) when the measurement result has fluctuated to values outside of a predetermined range.

Planar Structure of Detecting Elements

Figure 3:
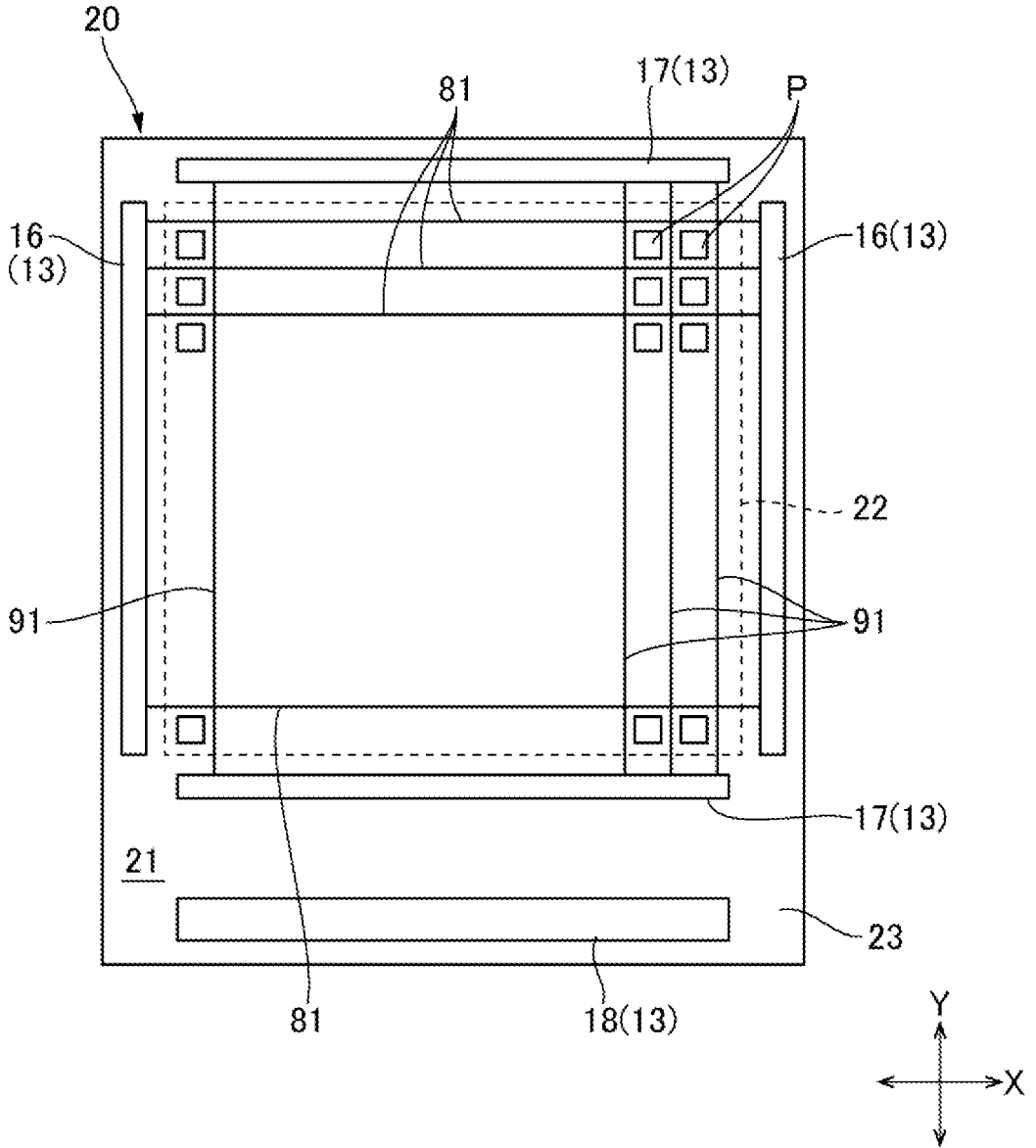
FIG. 3 is a plan view of a substrate on which detecting elements are arranged.

FIG. 3 is a plan view of the substrate 20 on which detecting elements P are arranged. The detecting device 3 includes the substrate 20 and a plurality of detecting elements P formed at the substrate 20. The substrate 20 has a rectangular first region 22 and a rectangular frame-shaped second region 23 surrounding the first region 22.

The plurality of detecting elements P are arranged in a matrix in the X and Y directions in the first region 22. The drive circuit 13 for driving each detecting element P is disposed in the second region 23. The drive circuit 13 includes two scan line drive circuits 16 disposed at positions that sandwich the first region 22 in the X direction, two signal line drive circuits 17 disposed in regions extending in the X direction in the second region 23, and a terminal portion 18. The terminal portion 18 is formed in a region opposite to the first region 22 across one of the two signal line drive circuits 17. The substrate 20 is electrically coupled to an external circuit such as the control device 5 through the terminal portion 18.

The substrate 20 has, for example, a size with a width of about 3 mm in the X direction and a width of about 4 mm in the Y direction. In this case, the first region 22 has a square shape with a side length of 2.6 mm. The number of detecting elements P arranged in the first region 22 is 2704 when the number of columns arranged in the X direction is 52 and the number of rows arranged in the Y direction is 52. The dimensions of the substrate 20 and the number of detecting elements P are not limited to these.

Figure 4:
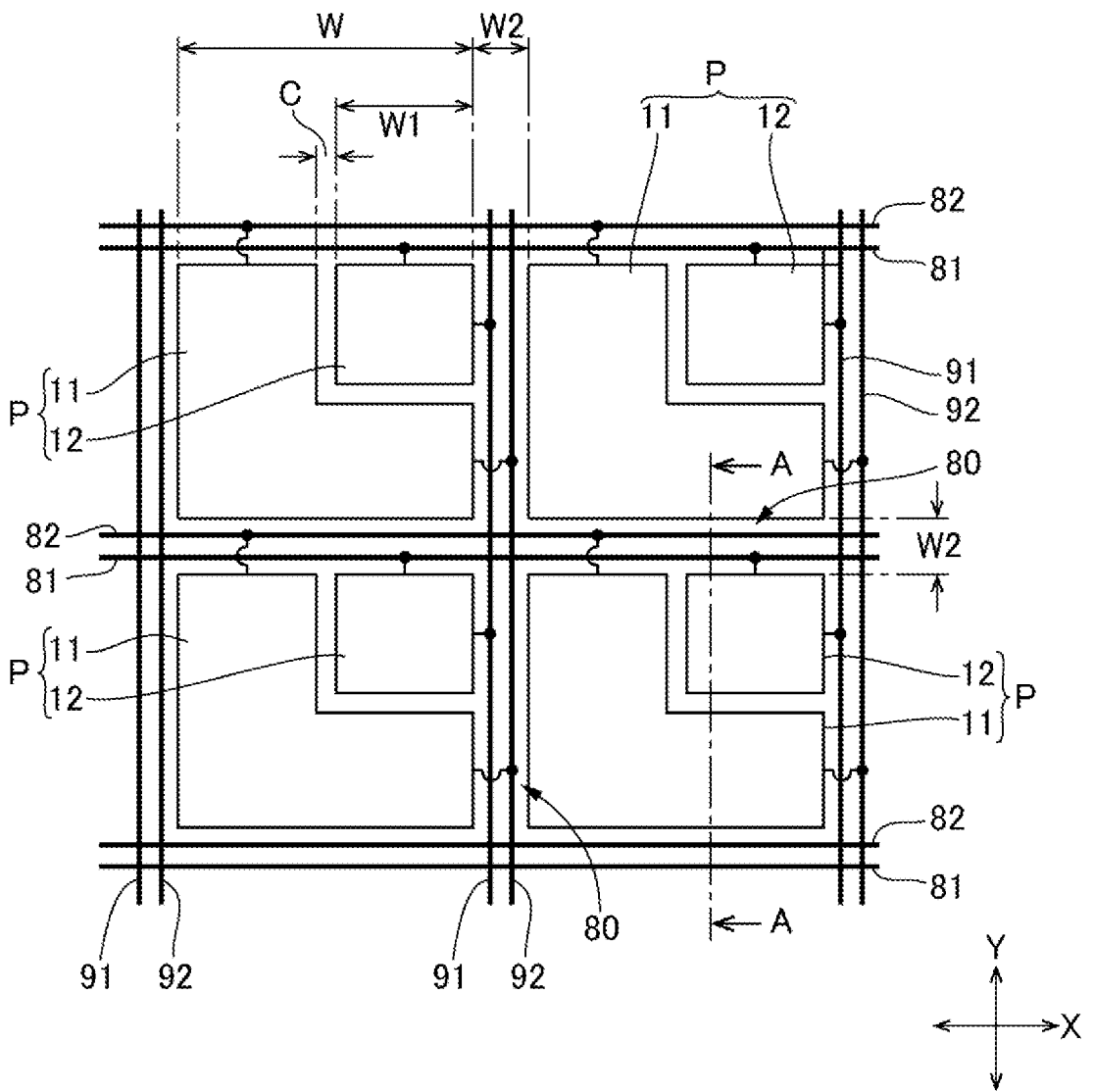
FIG. 4 is a plan view of detecting elements.

FIG. 4 is a plan view of detecting elements P, which is a partially enlarged view of the first region 22. As shown in FIGS. 3 and 4, a plurality of first scan lines 81 extending in the X direction and a plurality of first signal lines 91 extending in the Y direction are formed in the first region 22. One detecting element P is formed in each grid cell formed by the intersection of the first scan lines 81 and the first signal lines 91. A plurality of second scan lines 82 extending in the X direction and a plurality of second signal lines 92 extending in the Y direction are also formed in the first region 22. The first scan lines 81 and the second scan lines 82 are arranged in inter-element wiring regions 80 provided in gaps between detecting elements P adjacent to each other in the Y direction in the first region 22. The first signal lines 91 and the second signal lines 92 are also arranged in inter-element wiring regions 90 provided in gaps between detecting elements P adjacent to each other in the X direction. The second scan lines 82 and the second signal lines 92 are not shown in FIG. 3.

Each detecting element P includes one light receiving portion 11 and one light emitting portion 12 as described above. The drive circuit 13 drives the light emitting portions 12 of the plurality of detecting elements P in a time division manner. For example, the light emitting portions 12 of the plurality of detecting elements P are caused to emit light one by one in an arbitrary order. Each light emitting portion 12 is driven based on a potential supplied to a corresponding pair of a first scan line 81 and a first signal line 91. For example, the signal line drive circuit 17 selects the plurality of first signal lines 91 in an arbitrary order and supplies a potential corresponding to the light emission intensity of the light emitting portion 12 to the selected first signal line 91. On the other hand, the scan line drive circuit 16 selects the plurality of first scan lines 81 in an arbitrary order and supplies a potential to the selected first scan line 81. Thereby, a driving current is supplied to the light emitting portion 12 of the detecting element P corresponding to the intersection of the first signal line 91 and the first scan line 81 to which a potential has been supplied and thus the light emitting portion 12 emits light. The mode of driving the plurality of detecting elements P is not limited to the mode of driving them one by one.

Each light receiving portion 11 receives light having a wavelength emitted from a light emitting portion 12 disposed in the same element. A second scan line 82 and a second signal line 92 are electrically coupled to electrodes of each light receiving portion 11. Each light receiving portion 11 outputs a detection signal corresponding to the intensity of received light via the second signal line 92 when the light emitting portion 12 disposed in the same element has emitted light.

In each detecting element P, the light receiving portion 11 has a larger area than the light emitting portion 12. In the first embodiment, the detecting element P is rectangular. The light emitting portion 12 is rectangular and is disposed at a corner of the detecting element P. The light receiving portion 11 has a bent shape and is disposed surrounding two sides of the light emitting portion 12.

For example, the detecting element P has a square shape with a side length W of 45 μm. The light emitting portion 12 has a square shape with a side length W1 of 20 μm and a gap C (clearance) between the light receiving portion 11 and the light emitting portion 12 is 5 μm. A gap W2 between adjacent detecting elements P (the width of the inter-element wiring regions 80 and 90) is 5 μm. Thus, the arrangement pitch of the detecting elements P in the X and Y directions is 50 μm.

The shapes and dimensions of the light receiving portion 11 and the light emitting portion 12 are not limited to those described above. The side length of the detecting element P can be made smaller than 45 μm and the gap W2 between adjacent detecting elements P can be made smaller than 5 μm. The gap C (clearance) between the light emitting portion 12 and the light receiving portion 11 can be made smaller than 5 μm. For example, the side length of the detecting element P can be set to 10 μm and the gap W2 of the inter-element wiring regions 80 and 90 can be set to 1.5 μm. In this case, the side length W1 of the light emitting portion 12 can be set to 3 μm and the gap C (clearance) between the light emitting portion 12 and the light receiving portion 11 can be set to 1 μm. The shapes of the light emitting portion 12 and the light receiving portion 11 may each be a rectangle elongated in the Y direction and the light emitting portion 12 and the light receiving portion 11 may be arranged side by side in the X direction.

Cross-Sectional Structure of Detecting Element

Figure 5:
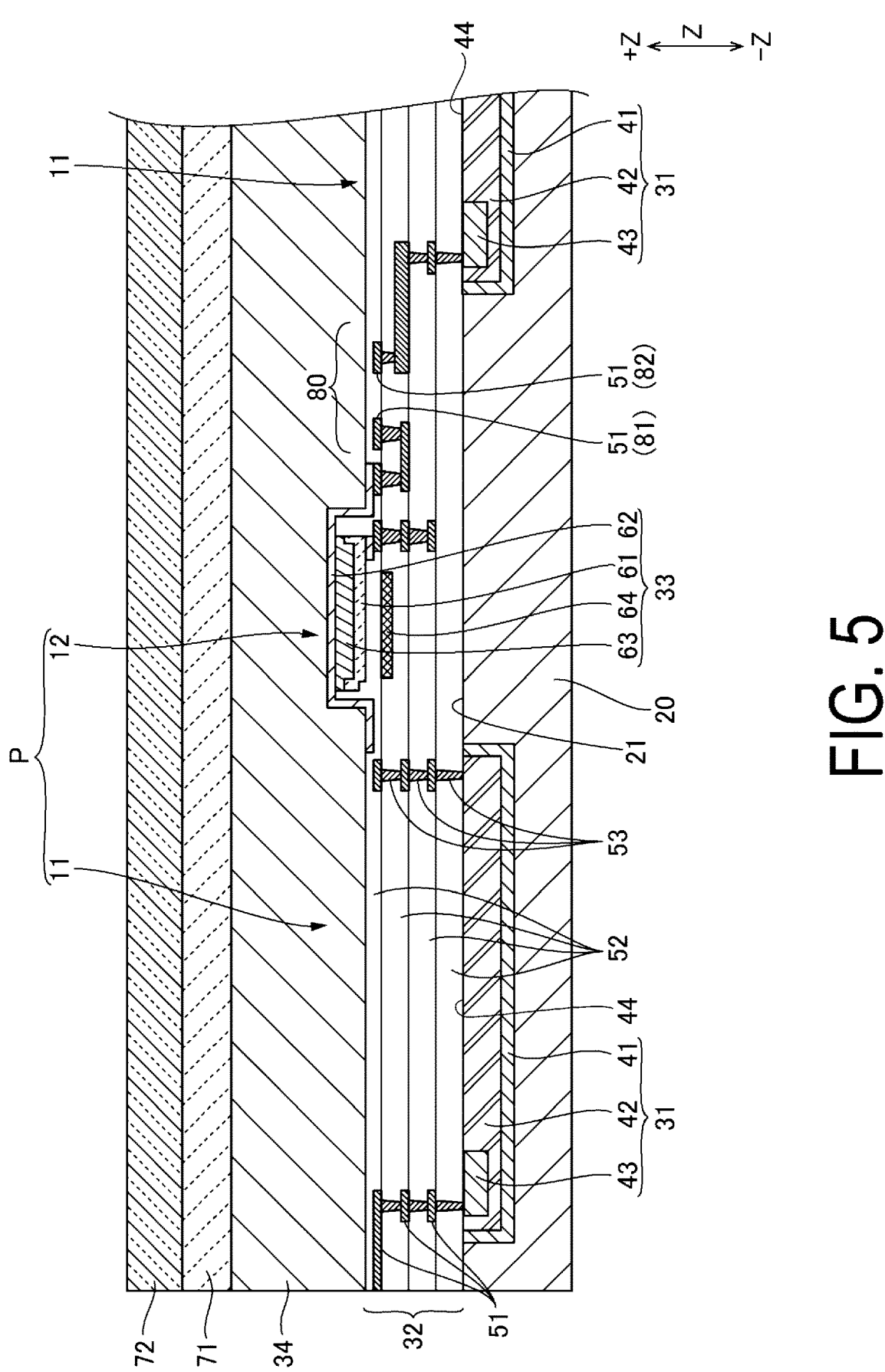
FIG. 5 is a cross-sectional view schematically showing a cross-sectional structure of a detecting element.

FIG. 5 is a cross-sectional view schematically showing a cross-sectional structure of a detecting element P, taken along line A-A of FIG. 4. As shown in FIG. 5, a direction normal to the substrate 20 coincides with the Z direction (the direction normal to the detecting surface 10). A first surface 21 is a surface facing in the +Z direction. A light receiving portion 11 and a light emitting portion 12 are formed at positions adjacent to each other on the first surface 21. An inter-element wiring region 80 is formed at a side of the light emitting portion 12 opposite to the light receiving portion 11.

The light receiving portion 11 includes a photoelectric conversion portion 31 that outputs a current corresponding to the intensity of received light. The light emitting portion 12 includes an organic electroluminescent (EL) light emitting element 33 using an organic material that emits light when supplied with a current. The substrate 20 is formed of a semiconductor material such as silicon (Si) and is used as a base (a substrate) on which the photoelectric conversion portion 31 and the organic EL light emitting element 33 are formed. The photoelectric conversion portion 31 and the organic EL light emitting element 33 are formed at positions adjacent to each other on the first surface 21 of the substrate 20.

The photoelectric conversion portion 31 is embedded in a surface layer of the substrate 20 on the first surface 21 side. The photoelectric conversion portion 31 includes a photodiode such as a PIN photodiode or a PN photodiode or a phototransistor. In the example shown in FIG. 5, the photoelectric conversion portion 31 includes an n-type semiconductor layer 41 embedded in the substrate 20, a p-type semiconductor layer 42 formed inside the n-type semiconductor layer 41, and an n-type semiconductor layer 43 buried inside the p-type semiconductor layer 42. The p-type semiconductor layer 42 is exposed on the first surface 21 of the substrate 20. The p-type semiconductor layer 42 forms a light receiving surface 44 on which light that has passed through wiring layers 32 formed at the first surface 21 is incident. The light receiving surface 44 is located on the same plane as the first surface 21 of the substrate 20.

The stack of wiring layers 32 includes conductive layers 51 made of a light-reflecting material such as an aluminum-copper alloy (AlCu) or titanium nitride (TIN), interlayer insulating films 52 made of a light-transmitting material such as silicon dioxide (SiO2) or silicon nitride (SiN), and conductive plugs 53 formed in the interlayer insulating film 52. The conductive plugs 53 are made of, for example, a light-absorbing material such as W (tungsten).

The conductive plugs 53 and the conductive layers 51 form wirings electrically coupled to an anode and a cathode (not shown) of the photoelectric conversion portion 31. The wirings coupled to the anode and cathode of the photoelectric conversion portion 31 extend to the inter-element wiring regions 80 and 90 in the stack of wiring layers 32.

The organic EL light emitting element 33 includes a first electrode 61 and a second electrode 62 that face each other in the Z direction and an organic light emitting layer 63 formed between the first electrode 61 and the second electrode 62. The organic light emitting layer 63 contains an organic material that emits light when supplied with a current. For example, the organic light emitting layer 63 contains a green light emitting material and light L emitted from the light emitting portion 12 is green light. The organic EL light emitting element 33 also includes a reflective layer 64 formed in the stack of wiring layers 32. The reflective layer 64 is formed at a position overlapping the organic light emitting layer 63 on the −Z direction side (that is, on the substrate 20 side) thereof. The reflective layer 64 is made of, for example, a light-reflecting material such as an aluminum copper alloy (AlCu).

The organic EL light emitting element 33 is a top emission type organic EL element capable of extracting light from the +Z side of the organic light emitting layer 63. The first electrode 61 is an anode. The first electrode 61 is a transparent electrode made of, for example, indium tin oxide (ITO). The second electrode 62 is a cathode. The second electrode 62 is, for example, a light-transmitting electrode made of a silver-magnesium alloy (AgMg). A light-blocking electrode may be used as the first electrode 61 of the organic EL light emitting element 33. In addition to the organic light emitting layer 63, a hole injection layer, a hole transport layer, an electron injection layer, and an electron transport layer may be provided between the first electrode 61 and the second electrode 62.

In a region of the stack of wiring layers 32 overlapping the organic EL light emitting element 33 in the Z direction, conductive plugs 53 and conductive layers 51 form wirings electrically coupled to the first electrode 61 and the second electrode 62. The wirings coupled to the first electrode 61 and the second electrode 62 extend to the inter-element wiring regions 80 and 90 in the stack of wiring layers 32.

The light emitting portion 12 includes a sealing layer 34 that covers the entirety of the organic EL light emitting element 33 from the +Z direction. The sealing layer 34 is made of, for example, a light-transmitting inorganic material such as silicon dioxide (SiO$_2$) or silicon nitride oxide (SiON). The sealing layer 34 may contain other materials to the extent that the sealing performance is not degraded. In the first embodiment, the sealing layer 34 is formed over all of the light emitting portion 12, the light receiving portion 11, and the inter-element wiring regions 80 and 90. In the light receiving portion 11 and the inter-element wiring regions 80 and 90, the sealing layer 34 is formed at the surface of the stack of wiring layers 32.

In the inter-element wiring region 80, two conductive layers 51 forming a first scan line 81 and a second scan line 82 are arranged in the stack of wiring layers 32. For example, the first scan line 81 is coupled to the second electrode 62 of the organic EL light emitting element 33 as shown in FIG. 5. The second scan line 82 is coupled to the photoelectric conversion portion 31.

The detecting element P and the inter-element wiring regions 80 and 90 are covered with a cover plate 72 via a transparent resin layer 71. A surface of the cover plate 72 on the +Z side forms the detecting surface 10. The cover plate 72 is optically transparent and can be made of, for example, a glass plate or a quartz plate. The transparent resin layer 71 is made of, for example, a transparent resin such as an epoxy resin or an acrylic resin.

Main Functions and Advantages of First Embodiment

As described above, the detecting device 3 of the first embodiment includes the substrate 20 and a plurality of detecting elements P arranged in a matrix at the substrate 20. Each of the plurality of detecting elements P includes a light emitting portion 12 that emits light toward the living body and a light receiving portion 11 that can receive light from the living body based on the light emitted from the light emitting portion 12. The light receiving portion 11 includes a photoelectric conversion portion 31 formed at the substrate 20. The light emitting portion 12 includes an organic EL light emitting element 33 formed at the substrate 20 at a position adjacent to the photoelectric conversion portion 31.

The measuring apparatus 100 of the first embodiment includes the detecting device 3 and the control device 5 as an information analysis unit that identifies biological information from a detection signal indicating the detection result of the detecting device 3.

In the detecting device 3 of the first embodiment, each of the plurality of detecting elements P arranged in a matrix includes a light emitting portion 12 and a light receiving portion 11 in the same element. Because the light receiving portion 11 and the light emitting portion 12 respectively include a photoelectric conversion portion 31 and an organic EL light emitting element 33 that are formed at the same substrate 20 as a base, the light emitting portion 12 (the photoelectric conversion portion 31) and the light receiving portion 11 (the organic EL light emitting element 33) can be arranged closer to each other than when an LED and a photodiode implemented as chips are mounted on a substrate as in the related art. Thus, the detecting element P can be reduced in size. Also, a plurality of detecting elements P can be arranged close to each other on the same substrate 20. Thus, the detecting device 3 can be reduced in size.

For example, in the detecting device 3 of the first embodiment, the area of the light receiving portion 11 is larger than the area of the light emitting portion 12. The gap C between the light receiving portion 11 and the light emitting portion 12 can be set to 5 μm or less. The detecting element P can be rectangular with a side length W of 45 μm or less. The gap W2 between adjacent detecting elements P can be set to 5 μm or less. The gap between the light receiving portion 11 and the light emitting portion 12 is in millimeters when an LED and a photodiode implemented as chips are mounted on a substrate as in the related art, but in the configuration of the first embodiment, the gap C between the light receiving portion 11 and the light emitting portion 12 is in microns and the outer dimension (the side length) of the detecting element P is also about several tens of μm. Thus, the size of the detecting device 3 can be reduced even when the detecting device 3 is constructed by arranging a plurality of detecting elements P in a matrix.

In the detecting device 3 of the first embodiment, each light receiving portion 11 receives light emitted from a light emitting portion 12 at a close position. When the light emitting portion 12 and the light receiving portion 11 are close to each other, the amount of received light, which has been returned to the light receiving portion 11 from the measuring site M after being emitted from the light emitting portion 12, is large. In particular, when the light L emitted from the light emitting portion 12 is green light, the green light returns after diffusing only to a shallow region in the body of the subject, such that the amount of received light rapidly decreases away from the light emitting portion 12. Thus, by bringing the light receiving portion 11 and the light emitting portion 12 close to each other, it is possible to increase the amount of received light when the light L emitted from the light emitting portion 12 is green light. The amount of received light is also large because the area of the light receiving portion 11 is larger than the area of the light emitting portion 12.

Further, when the light emitting portion 12 and the light receiving portion 11 are close to each other, light that the light receiving portion 11 can receive out of light emitted in all directions from the light emitting portion 12 is light that has been emitted at angles close to the direction normal to the detecting surface 10 and incident at angles close to the normal direction. Thus, the light receiving portion 11 can receive linear light that easily passes through the living body out of light emitted from the light emitting portion 12, such that the loss of light is small. The light receiving portion 11 can receive linear light, for example, when the gap C between the light receiving portion 11 and the light emitting portion 12 is 5 μm or less as described above.

When linear light is received by the light receiving portion 11, it is less likely to include noise such as external light. In the first embodiment, a plurality of detecting elements P arranged in a matrix are provided and only some of the plurality of detecting elements P can be driven to perform measurement. Thus, it is also possible to reduce noise by driving a detecting element(s) P on the substrate in a central region thereof where external light is less likely to be incident.

The amount of received light can be increased and the loss of light can be reduced in this way, such that a necessary amount of received light can be secured even if the amount of light emitted from the light emitting portion 12 is small and thus power consumption of the light emitting portion 12 can be reduced. Thus, it is possible to achieve power saving in the detecting device 3. In addition, the S/N ratio can be increased because a large amount of light returning from the measuring site M can be received and noise is small. Thus, the measuring apparatus 100 can identify biological information from the detection signal S with a high S/N ratio, such that it is possible to increase the measurement accuracy.

While an angle limiting filter or a bandpass filter is provided on the light receiving portion 11 to deal with noise in the related art, the detecting device 3 of the first embodiment can obtain a detection signal S with a high S/N ratio without providing a filter layer because noise included in light incident on the light receiving portion 11 is small. By eliminating the filter layer, it is possible to reduce the height (thickness) of the detecting element P in the direction normal to the substrate 20 (that is, the Z direction). Thus, it is possible to reduce the thickness of the detecting device 3.

In the detecting device 3 of the first embodiment, a plurality of first scan lines 81 extending parallel to the X direction (a first direction) and a plurality of first signal lines 91 and second signal lines 92 extending parallel to the Y direction (a second direction) intersecting the X direction are formed at the substrate 20. each one of detecting elements P is disposed in each of areas obtained by partitioning the substrate 20 in a grid pattern by the first scan lines 81 and the first signal lines 91. The light emitting portion 12 is driven via a first scan line 81 and a first signal line 91. The light receiving portion 11 outputs a detection signal via a second signal line 92. Thus, the detecting device 3 can have a structure that uses the pixel structure of an organic EL display panel. The light emitting portion 12 of each detecting element P can be driven using the pixel driving method of an organic EL display panel.

In the light emitting portion 12 of the first embodiment, the first electrode 61 and the second electrode 62 of the organic EL light emitting element 33 are coupled respectively to the first scan line 81 and the first signal line 91. That is, the light emitting portion 12 has an organic EL element structure driven by a passive matrix system rather than disposing a driving element such as a switching transistor in each detecting element P. Thus, the structure of the light emitting portion 12 is simple, such that the detecting device 3 can be manufactured easily.

In the detecting device 3 of the first embodiment, a second scan line 82 extending in the X direction (the first direction) and a second signal line 92 extending in the Y direction (the second direction) are provided on the substrate 20 corresponding to each of the plurality of detecting elements P. Each light receiving portion 11 is electrically coupled to a second scan line 82 and a second signal line 92 and outputs a detection signal via the second signal line 92. Thus, the detecting device 3 can output a detection signal from each light receiving portion 11 using the same wiring structure as that with scan lines and signal lines for driving pixels.

In the first embodiment, the light emitting portion 12 of each detecting element P is rectangular. The light receiving portion 11 of each detecting element P has a bent shape and is disposed surrounding two sides of the light emitting portion 12. With such a shape, it is easy to connect light receiving portions 11 and light emitting portions 12 to scan lines and signal lines arranged in a grid pattern.

The detecting device 3 of the first embodiment includes the drive circuit 13 that supplies a drive current to each light emitting portion 12 and the drive circuit 13 drives a plurality of detecting elements P, for example, in a time division manner. By doing so, the detecting device 3 can be used without continuously driving the detecting elements P, such that heat generation of the detecting elements P can be reduced. This can prevent deterioration of the detecting element P, such that the life of the detecting device 3 can be extended. Power consumption can also be reduced because the number of detecting elements P driven simultaneously can be reduced.

2. Second Embodiment

Figure 6:
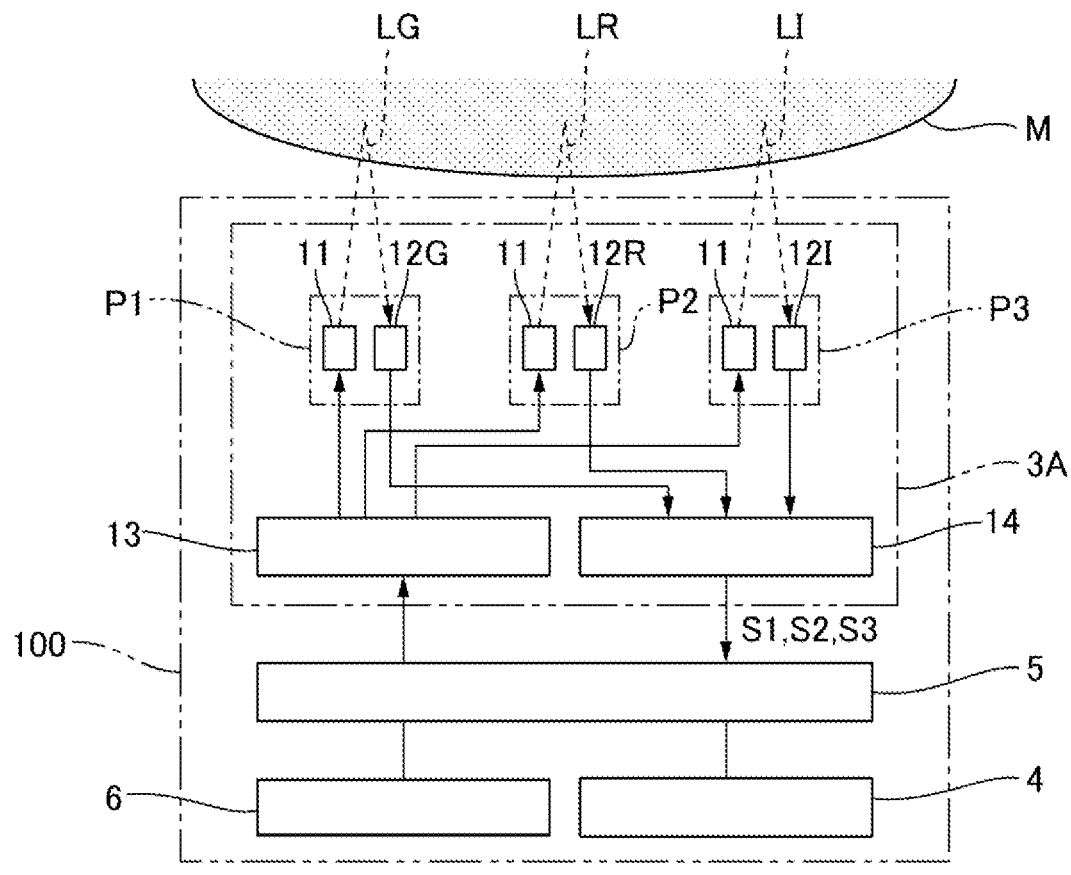
FIG. 6 is a block diagram showing functional components of a measuring apparatus of a second embodiment.

FIG. 6 is a block diagram showing functional components of a measuring apparatus 100 of a second embodiment. As shown in FIG. 6, the measuring apparatus 100 includes a control device 5, a storage device 6, a display device 4, and a detecting device 3A. The detecting device 3A differs from that of the first embodiment in that it includes three types of detecting elements, that is, first detecting elements P1, second detecting elements P2, and third detecting elements P3, as detecting elements in each of which a light receiving portion and a light emitting portion are paired. The three types of detecting elements have the same configuration as those of the first embodiment, except for wavelengths of light emitted from their organic light emitting layers.

Figure 7:
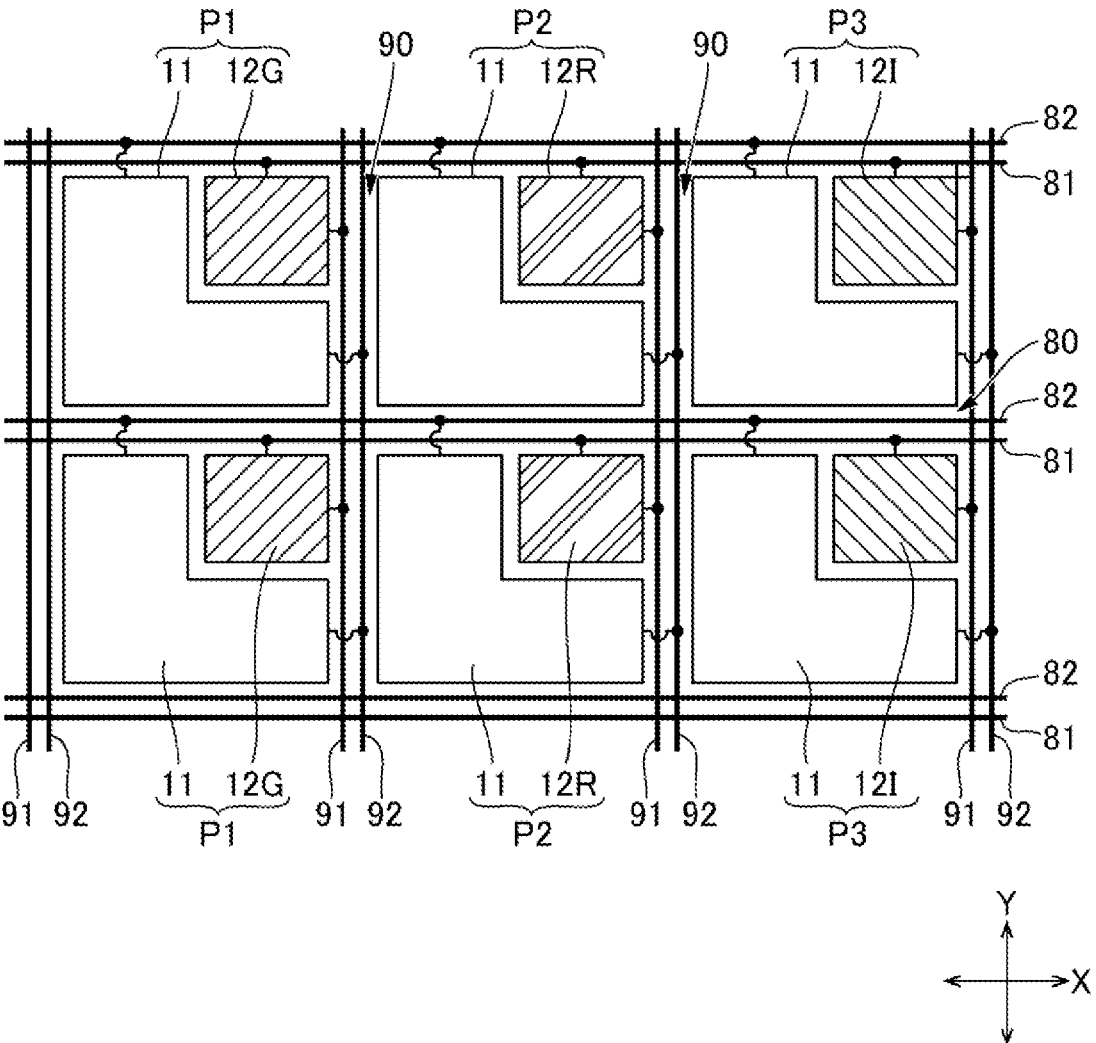
FIG. 7 is a plan view of a first detecting element, a second detecting element, and a third detecting element.

FIG. 7 is a plan view of a first detecting element P1, a second detecting element P2, and a third detecting element P3. The detecting device 3 includes a substrate 20 on which first detecting elements P1, second detecting elements P2, and third detecting elements P3 are arranged in a matrix in X and Y directions. Each of the first detecting elements P1 includes a light receiving portion 11 and a light emitting portion 12G. Each of the second detecting elements P2 includes a light receiving portion 11 and a light emitting portion 12R. Each of the third detecting elements P3 includes a light receiving portion 11 and a light emitting portion 121. The light emitting portion 12G, the light emitting portion 12R, and the light emitting portion 121 emit light of different wavelengths through the detecting surface 10.

The light emitting portion 12G emits first light LG. The first light LG is, for example, green light having a green wavelength band of 520 nm to 550 nm and a peak wavelength of 520 nm. Thus, the light emitting portion 12G includes an organic light emitting layer containing a green light emitting material. The light emitting portion 12R emits second light LR. The second light LR is, for example, red light having a red wavelength band of 600 nm to 800 nm and a peak wavelength of 660 nm. Thus, the light emitting portion 12R includes an organic light emitting layer containing a red light emitting material. The light emitting portion 121 emits third light LI. The third light LI is, for example, near-infrared light having a near-infrared wavelength band of 800 nm to 1300 nm. The third light LI is, for example, light with a peak wavelength of 905 nm. Thus, the light emitting portion 121 includes an organic light emitting layer containing a near-infrared light emitting material. The wavelengths of light emitted from the light emitting elements are not limited to those of the above wavelength bands.

A drive circuit 13 of the detecting device 3A supplies a driving current to each of the light emitting portion 12G, the light emitting portion 12R, and the light emitting portion 121 to cause them to emit light. For example, the drive circuit 13 periodically drives the first detecting element P1, the second detecting element P2, and the third detecting element P3 in a time division manner to periodically cause the light emitting portion 12G, the light emitting portion 12R, and the light emitting portion 121 to emit light in a time division manner.

An output circuit 14 generates a plurality of detection signals S1, S2, and S3 corresponding to the different wavelengths based on detection signals generated by the light receiving portions 11 of the first detecting element P1, the second detecting element P2, and the third detecting element P3. The detection signal S1 is a signal representing the intensity of received light when the light receiving portion 11 of the first detecting element P1 has received the first light LG (green light). The detection signal S2 is a signal representing the intensity of received light when the light receiving portion 11 of the second detecting element P2 has received the second light LR (infrared light). The detection signal S3 is a signal representing the intensity of received light when the light receiving portion 11 of the third detecting element P3 has received the third light LI (near-infrared light).

The control device 5 executes a program stored in a storage device 6 to identify biological information of the subject from the plurality of detection signals S1, S2, and S3 generated by the detecting device 3. Specifically, the control device 5 can identify the pulse rate of the subject by identifying the heartbeat of the subject from the detection signal S1 representing the received light intensity of the first light LG (green light), similar to the first embodiment. Further, in the second embodiment, the control device 5 can identify the oxygen saturation (SpO$_2$) of the subject by analyzing the detection signal S2 representing the received light intensity of the second light LR (red light) and the detection signal S3 representing the received light intensity of the third light LI (near-infrared light).

The first detecting element P1, the second detecting element P2, and the third detecting element P3 differ only in the organic light emitting layers of the light emitting portion 12G, the light emitting portion 12R, and the light emitting portion 121 and their light receiving portions 11 have the same configuration. The light receiving portions 11 can be made common even when their wavelength bands of received light differ because the light receiving portions 11 do not require a filter layer to deal with noise as described above.

While the second embodiment includes three types of detecting elements, two types of detecting elements may also be arranged in a matrix with either the second detecting elements P2 or the third detecting elements P3 omitted.
Modifications (1) In each of the above embodiments, each detecting element P is configured to drive the organic EL light emitting element 33 by a passive matrix system, but it may also be configured to drive the organic EL light emitting element 33 by an active matrix system. For example, a switching transistor can be formed at a position overlapping the organic EL light emitting element 33 in the Z direction in a layer of the substrate 20. It is desirable to provide an anode wiring coupled to the first electrode 61 and a cathode wiring coupled to the second electrode 62 separately from the first scan line 81 and the first signal line 91. In this case, it is desirable to use the first scan line 81 and the first signal line 91 as control lines for controlling on/off of the switching transistor. This enables more active control of the timing of light emission and the amount of light emission of each of the plurality of organic EL light emitting elements 33.

(2) In addition to modification (1), each detecting element P may be configured to include a switching element on a wiring electrically coupled to the anode or the cathode of the photoelectric conversion portion 31 of the light receiving portion 11. Further, it is desirable that the second scan line 82 be a control line for controlling on/off of the switching element. This enables more active control of the plurality of light receiving portions 11, more effectively reducing power consumption and suppressing noise. When the first scan line 81 and the second scan line 82 are used as control lines, the first scan line 81 and the second scan line 82 can be made common. That is, the switching element is coupled to the first scan line 81 and can be configured to control output of the detection signal via the second signal line 92.

(3) In each detecting element, the light emitting portion may be configured to include a color filter overlapping the organic light emitting layer. For example, the light emitting portion 12G may be configured to include a color filter that selectively transmits light in a wavelength band corresponding to the first light LG (green light), the light emitting portion 12R may be configured to include a color filter that selectively transmits light in a wavelength band corresponding to the second light LR (red light), and the light emitting portion 12I may be configured to include a color filter that selectively transmits light in a wavelength band corresponding to the third light LI (near-infrared light). The color filters are formed, for example, on a surface of the sealing layer 34 on the +Z side. By adding the color filters, it is possible to increase the color purity of the first light LG (green light), the second light LR (red light), and the third light LI (near-infrared light) emitted from the light emitting portions 12G, 12R, and 12I.

When the configuration in which color filters are provided, the organic light emitting layer can be made of an organic material that emits white light.

What is claimed is:

1. A detecting device comprising a substrate and a plurality of detecting elements arranged in a matrix at the substrate, wherein each of the plurality of detecting elements includes a light emitting portion configured to emit light toward a living body and a light receiving portion configured to receive light from the living body based on the light emitted from the light emitting portion, the light receiving portion includes a photoelectric conversion portion formed at the substrate, and the light emitting portion includes an organic electroluminescent light emitting element formed at the substrate at a position adjacent to the photoelectric conversion portion, wherein a plurality of first scan lines extending in a first direction and a plurality of first and second signal lines extending in a second direction intersecting the first direction are formed at the substrate, each one of detecting elements is disposed in each of areas obtained by partitioning the substrate in a grid pattern by the first scan lines and the first signal lines, the light emitting portion is configured to be driven via the first scan line and the first signal line, and the light receiving portion is configured to output a detection signal of the light emitted from the living body through the second signal line.

2. The detecting device according to claim 1, wherein a first electrode and a second electrode of the organic electroluminescent light emitting element are coupled respectively to the first scan line and the first signal line.

3. The detecting device according to claim 1, wherein the light emitting portion includes a switching transistor, and the switching transistor is coupled to the first scan line and the first signal line and the first electrode and the second electrode of the organic electroluminescent light emitting element are coupled respectively to an anode wiring and a cathode wiring.

4. The detecting device according to claim 3, wherein the light receiving portion includes a switching element, and the switching element is coupled to the first scan line and controls output of the detection signal via the second signal line.

5. The detecting device according to claim 3, wherein the substrate includes a second scan line extending in the first direction, the light receiving portion includes a switching element, and the switching element is coupled to the second scan line and controls output of the detection signal via the second signal line.

6. The detecting device according to claim 1, wherein the plurality of detecting elements include a first detecting element and a second detecting element, the light emitting portion provided in the first detecting element is configured to emit first light, and the light emitting portion provided in the second detecting element is configured to emit second light having a longer wavelength than the first light.

7. The detecting device according to claim 6, wherein the first light is light in a green wavelength band, and the second light is light in a red wavelength band or a near-infrared wavelength band.

8. The detecting device according to claim 1, further comprising a drive circuit configured to supply a drive current to the light emitting portion, wherein the drive circuit is configured to drive the plurality of detecting elements in a time division manner.

9. The detecting device according to claim 1, wherein an area of the light receiving portion is larger than an area of the light emitting portion, and a gap between the light receiving portion and the light emitting portion is 5 μm or less.

10. The detecting device according to claim 9, wherein each of the detecting elements has a rectangular shape with a side length of 45 μm or less, and a gap between adjacent ones of the detecting elements is 5 μm or less.

11. The detecting device according to claim 1, wherein the light emitting portion is rectangular, the light receiving portion has a bent shape and is disposed surrounding the light emitting portion.

12. A measuring apparatus comprising:

the detecting device according to claim 1; and an information analysis unit configured to identify biological information from a detection signal indicating a detection result of the detecting device.

* * * * *